United States Patent [19]

Cohen

[11] Patent Number: 5,017,000
[45] Date of Patent: May 21, 1991

[54] MULTIFOCALS USING PHASE SHIFTING

[76] Inventor: Allen L. Cohen, 10108 Windsong Ter., Richmond, Va. 23233

[21] Appl. No.: 863,069

[22] Filed: May 14, 1986

[51] Int. Cl.$^5$ .................. G02B 27/44; G02B 5/18; G02C 7/04; A61F 2/16

[52] U.S. Cl. .................. 351/161; 350/162.16; 350/162.20; 350/162.22; 350/162.23; 350/437; 350/452; 351/159; 351/168; 351/171; 623/6

[58] Field of Search ........ 351/159, 161, 168, 169–172; 350/162.22, 162.2, 162.21, 162.23, 162.24, 162.16, 437, 452; 623/6

[56] References Cited

U.S. PATENT DOCUMENTS

| 4,016,416 | 4/1977 | Shepherd, Jr. et al. ... 350/162.16 X |
| 4,210,391 | 7/1980 | Cohen .......................... 350/452 X |
| 4,338,005 | 7/1982 | Cohen .......................... 350/452 X |
| 4,340,283 | 7/1982 | Cohen .......................... 351/161 |
| 4,637,697 | 1/1987 | Freeman ....................... 350/452 X |

OTHER PUBLICATIONS

Genovese et al.; "Phase Plate Lens for a Multiple Image Lens System"; *IBM Tech. Discl. Bulletin;* vol. 8, No. 12; May 1966; pp. 1796–1797.

*Primary Examiner*—Scott J. Sugarman
*Attorney, Agent, or Firm*—George A. Skoler

[57] ABSTRACT

This invention relates to a multifocal optical lens configuration that relies on the phenomenon of simultaneous vision whereby the eye is presented with two clear images at once. In particular this invention allows a lens to be made with arbitrary relative brightnesses between the multiple images.

17 Claims, 7 Drawing Sheets

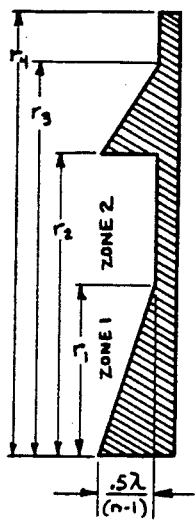
Fig. 1
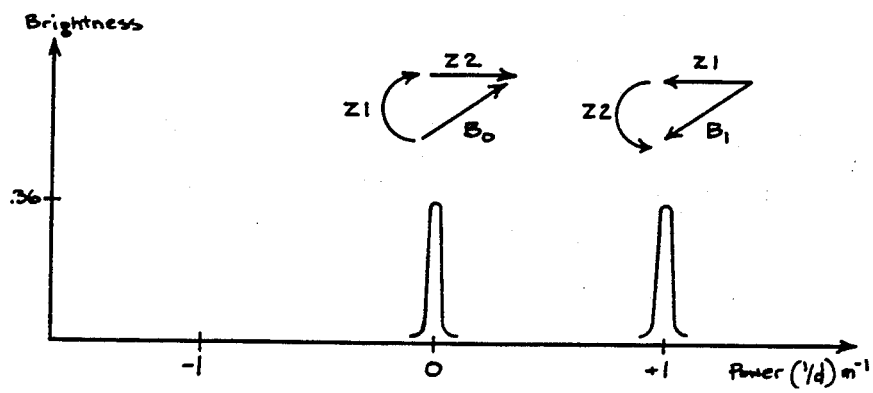
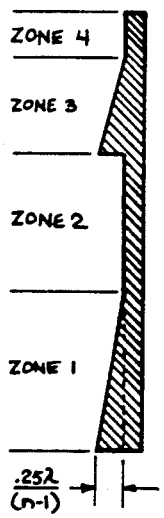
Fig. 2
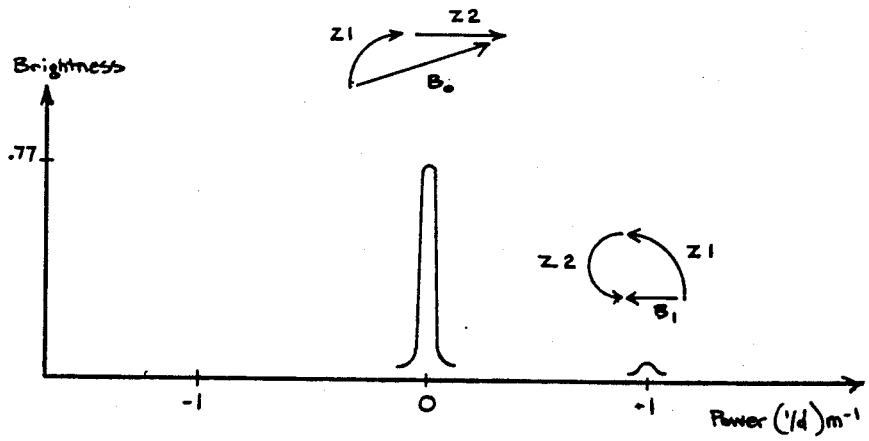

$Z1(1) = \sqrt{2}/\pi$
$Z2(1) = 1/\pi$
$a(1) = 45°$ $B_1^2 \approx 0.1$ $Z1(0) = \sqrt{2}/\pi$
$Z2(0) = 1/2$
$a(0) = 135°$ $B_0^2 \approx 0.77$ $B_1^2 = Z1_1^2 + Z2_1^2 - 2(Z1_1)(Z2_1)\cos[45+b]$ $B_0^2 = Z1_0^2 + Z2_0^2 - 2(Z1_0)(Z2_0)\cos[135-b]$ $b = 56.64°$ (i.e. $b/360 = .157$)
$B_0^2 = B_1^2 = 0.36$

MULTIFOCALS USING PHASE SHIFTING

BACKGROUND OF THE INVENTION

The design of bifocal eyeglasses makes use of the principle of alternating vision. That is, the eye alternates between two adjacent lenses of different focal power. This approach has not been as successfull in contact lenses, because of the tendency of a contact lens to move with the eye. To overcome this problem, many of the bifocal contact lenses being used today, rely on the phenomenon of simultaneous vision, whereby the eye is presented with two clear images at once. This is achieved, as described for example by DeCarle in his U.S. Pat. No. 3,037,425, by using a central lens, smaller in diameter than the pupil of the eye, surrounded by an annular lens of a differing power. This can be successfull only when the relative brightnesses of the two images remain constant. Unfortunately, in current lens designs, as the pupil of the eye normally changes its diameter, the relative image brightnesses, provided by the two concentric lenses, shift with respect to each other.

A more recent bifocal lens configuration, makes use of a zone plate design as described in my U.S. Pat. Nos. 4,210,391, 4,338,005 and 4,340,283. These designs allow the two different focal powers to be achieved by diffractive effects. However, because these lens designs utilize multiple concentric rings of diameters less than that of the pupil of the eye, as the pupil of the eye opens and closes, only a small number of rings are involved and the relative brightnesses of the two images remain the same.

But even though these lenses maintain a constant ratio of relative image brightnesses between the different focal points, independent of entrance pupil size, this constant is not always satisfactory. We see for example, in FIG. 1, a blazed zone plate bifocal designed according to my U.S. Pat. No. 4,340,283 wherein the zone radii r(k) are given by $$r(k) = \sqrt{k*\lambda*d},$$

with $\lambda$ the design wavelength, and d the design focal point. In this case the two image brightnesses are equal (i.e. a 1:1 ratio), because the odd zone blaze was chosen to vary linearly to a depth equal to one-half wavelength ($\lambda/2$) so that the odd zone focal power Fo is equal to $1/d$, while the even zones have no blaze in order that the even zone power Fe is equal to zero. This is in accordance with my U.S. Patent wherein it is specified that $1/d = Fo - Fe$. However, if we consider FIG. 2, a blazed zone plate with a blaze depth of only one-quarter wavelength, a lens which may be easier to manufacture than the lens of FIG. 1, we see that the image brightnesses are unequal limiting the use of this lens as an ophthalmic bifocal.

SUMMARY OF THE INVENTION

The invention relates to a multiple focal point profiled phase plate having a plurality of annular concentric zones spaced according to the formula $$r(k) = \sqrt{constant \times k},$$

where r(k) is the zone radii and k is a zone; in which a repetitive step is incorporated in the profile and has an optical path length greater or less than one-half wavelength.

A multiple focal power optical device comprising: body means having a plurality of annular concentric zones spaced so as to produce a diffractive power; wherein a phase shifting means is incorporated into at least some of the annular zones, the phase shifting means being of a step function nature, causing a substantially constant shift in the optical path length across essentially the entire zone into which it is incorporated.

An embodiment of the invention employs body means which comprise an optically refracting material. The phase shifting means may include the body means together with imbedded contaminants to achieve the desired phase shift, or an excavated portion of the body means. The phase shifting means may occupy every alternate zone.

The invention features the use of phase shifting means that are adjusted so as to cause equal image brightness at each of the focal points of said body means. The phase shifting steps may be adjusted so as to create a trifocal with equal image brightnesses at each of the focal points of said body means. In a preferred embodiment, the phase shifting steps are adjusted so as to cause the lens to focus some wavelengths of light preferentially. It is desirable to have the phase shifting steps adjusted so as to reduce the maximum depths of any blaze or step.

The invention employs an optical device as a contact lens, a spectacle lens, an intraocular lens implant, or a mirror.

A multiple focal point profiled phase plate, wherein a repetitive step is incorporated into the profile, whereby to cause a constant shift in the optical path length across essentially the entire zone into which it is incorporated. The phase plate is designed to operate as a multifocal lens in the visible light range. Such embodiments of the invention design the body means of said phase plate as a contact lens or as a camera lens.

In a multifocal lens we wish to share the incident light between the various focal points. It is important when doing this, that we keep the various image brightnesses at each of the focal points substantially equal in intensity. The present invention makes use of the fact that in multifocals that utilize diffraction lens designs, the radii of the zones substantially obey the formula that is given by $$r(k) = \sqrt{constant*k}.$$

That is, the annular zones are spaced so as to introduce phase shifts of an integral number of half-wavelengths. In these cases, we may completely analyze the lens by looking at just a small number of zones which form the repetitive pattern for the entire lens. For example, in FIGS. 1 and 2, we need examine only the first two zones (i.e. zones 1 and 2).

We will start by considering a phase plate analysis of monofocal lenses. Let us start with a flat lens of zero power divided into concentric half-wave zones as shown in FIG. 3. Now by cutting a half-wave step into the odd zones, we phase shift the light passing through these odd zones by precisely one-half wavelength creating the bifocal of FIG. 4. This was first proposed by R. W. Wood in his book "Physical Optics", Macmillan Co., N.Y. 1914, pgs. 37-40, 217, and 218. He used this technique to cause a brightening of the classical Rayleigh zone plate, and only considered one-half wavelength phase shifts.

We continue the analysis of monofocal phase plates by referring to FIG. 5, where we have a +1.0 Diopter monofocal configured in the usual way by cutting blazes one-wavelength deep, where a blaze is taken to be an angled cut as opposed to a flat step cut. Again, by the method of R. W. Wood, we can cut a half-wave step out of each of the odd zones (dotted regions of FIG. 5), in order to phase shift the light passing through these odd zones. The result is the bifocal phase plate of FIG. 6. However, while it is not obvious that a consideration of phase shift steps other than one-half wavelength would have any value or application to half-wave zone plates, this analysis will demonstrate some unique and unexpected results that are obtained by consideration of just such phase shift steps.

First let us return to the lens of FIG. 2, where the image brightness at 0.0 Diopters is greater than the image brightness at +1.0 Diopters. At 0.0 Diopters the phase change in light passing through the zones is caused only by the blazing. At 1.0 Diopter the phase change in light passing through the zones is shifted by one-half wavelength in addition to the phase shift caused by the blazing. First, considering the focus at 0.0 Diopters and the fact that zone 1 has a blaze depth of one-quarter wavelength, the amplitude vector $z1(0)$ for light passing through this zone is turned back 90 degrees (negative one-quarter wavelength). And since zone 2 has no blaze, the amplitude vector $z2(0)$ for light passing through this zone is not shifted at all. Finally, the phase angle $a(0)$ between the two resultant amplitude vectors is 135 degrees, yielding the image brightness $B_0^2$ at the 0.0 Diopter focus. At the 1.0 Diopter focus the amplitude vector $z1(1)$ for light passing through zone 1 is turned ahead by 90 degrees, while the amplitude vector $z2(1)$ for light passing through zone 2 is turned ahead by 180 degrees. And the phase angle $a(1)$ between the two resultant amplitude vectors is 45 degrees, yielding the image brightness $B_1^2$ at the 1.0 Diopter focus. All of this is shown in FIG. 7a, where the image brightnesses are calculated as the vector sum of the resultant amplitude vectors $z1$ and $z2$. Since we are considering two zones, it is convenient to assign the value $\frac{1}{2}$ to the total arc length of the small differential amplitude vectors passing through each zone. Thus, at the 0.0 Diopter focus, we have for the light amplitude vector $z1(0)$, of light passing through zone 1, $$z1(0) = \sqrt{2}/\pi.$$

Similarly, we have $z2(0) = \frac{1}{\pi}$, and for the phase angle $a(0)$ between the vectors $z1(0)$ and $z2(0)$, $a(0) = 135$ degrees. The resultant brightness is given by $B_0^2 = 0.77$. By the same reasoning, at the 1.0 Diopter focus we have, $$z1(1) = \sqrt{2}/\pi, z2(1) = 1/\pi,$$

with $a(1) = 45$ degrees, and $B_1^2 = 0.10$.

Now by cutting a step into the even zones, we can phase shift the light passing through the even zones by an amount depending on the depth of the step. The present invention makes use of the effects of an arbitrary phase shift, not necessarily equal to one-half wavelength. FIG. 7b shows the light amplitude vectors $z1$ and $z2$, representing the light from zone 1 and zone 2 respectively, for each focus separated by an additional phase shift of $b$ degrees. The resultant brightnesses $B_0^2$ at the 0.0 Diopter focus, and $B_1^2$ at the 1.0 Diopter focus are also shown. In FIG. 7b we see that as we increase the phase angle $b$ (by increasing the step depth), the dimmer image B becomes brighter, while the brighter image B becomes dimmer. Clearly there is a precise phase shift wherein the image brightnesses will be equal. In this particular case a phase shift of 0.157 wavelengths accomplishes the task, and FIG. 7c shows just such a resultant lens. It should also be noticed that the maximum depth of the facets in this lens is only 0.407 wavelengths deep. Typically, diffractive lenses require phase shifts of 0.5 wavelengths or more. It is an advantage to be able to reduce the required maximum phase shift, since many manufacturing techniques (i.e. ion implantation) are limited in the maximum phase shift they can achieve. It must of course be stated, that this is just one particular example of the use of a phase shifting step, and that in general we may choose phase shifting steps other than 0.157 wavelengths.

It is also interesting to consider application of this invention to lenses that utilize focal points symmetrically disposed about 0.0 Diopters, as described in my U.S. Pat. No. 4,338,005. FIG. 8 shows an example of this type of lens. This particular lens is an example of a trifocal with focii of unequal brightnesses. In this particular case by using a phase shift step of 0.212 wavelengths, we are able to construct the equal brightness trifocal of FIG. 9.

With reference to trifocals, we reconsider the flat lens of zero power shown in FIG. 3, as a degenerate trifocal with focii of unequal brightnesses. Indeed, two of the focii in this case exhibit zero brightness. Nevertheless, we can still apply the principles of this invention. FIG. 10 shows the resulting trifocal. An important advantage of this trifocal is its simple step design which allows for easier fabrication, since etching a step is much easier than cutting a blaze in many manufacturing techniques (i.e. ion reactive etching). While the bifocal lens of R. W. Wood is of a simple step design, this is the first trifocal of such a simple design. It should be clear from the foregoing analysis, that whenever a phase shift of x-wavelengths produces a satisfactory lens, we will also get a complimentary lens by using a phase shift of $(1.0 - x)$-wavelengths. FIG. 11 shows the trifocal complimentary to the one shown in FIG. 10.

Up to this point, we have only considered monochromatic light. If the lenses of FIGS. 10 and 11 were designed for a particular wavelength of light, for example yellow light, then the chromatic aberration inherent in diffractive lenses will produce the brightness distributions for red(R), yellow(Y), and blue(B) light as also shown in FIGS. 10 and 11. In addition to the chromatic aberration in focus, we also see a chromatic aberration in brightness. However, the chromatic aberration in brightness is usually opposite in complimentary lenses. This allow us to design composite lenses, such as that of FIG. 12, where we can reduce greatly the chromatic aberration in brightness.

Given the chromatic aberration in brightness that is inherent in lenses utilizing diffractive power, we can also design lenses that preferentially transmit particular wavelengths of our choice. For example, looking at the lens of FIG. 13, we have a trifocal lens that favors blue light at its 0.0 Diopter focus, and favors red light at its +1.0 Diopter and −1.0 Diopter focii. We can now use a phase shift step of 0.5-wavelengths to eliminate the focus at 0.0 Diopters, and we are left with the bifocal lens shown in FIG. 14, that attenuates blue light while favorably focussing red light. This of course would be advantageous to aphakic and other patients who need to be spared as much blue light as possible.

In view of the foregoing, it is a primary object of this invention to adjust the ratio of image brightnesses at the different focii of diffractive multifocal lenses.

It is another object of this invention to equalize the brightnesses at the different focii of those diffractive multifocal lenses with inherently unequal brightnesses.

It is another object of this invention to reduce the maximum phase shifts needed to create a diffractive multifocal lens.

It is still another object and advantage of this invention to simplify the construction of some diffractive multifocal lenses by replacing a blaze with a step.

And it is a further object and advantage of this invention, to allow the manipulation of chromatic aberration of brightness so as to create lenses that favor one wavelength over another.

Other objects and advantages of the present invention will be more fully apparent from the following description of the preferred embodiments when taken in conjunction with the accompanying drawings.

BRIEF DESCRIPTION OF THE DRAWINGS

FIG. 1 shows a portion of a profile of a typical phase plate bifocal, and its corresponding graph of brightness vs focal power, showing equal brightnesses (i.e. $B_0^2 = B_1^2$) at each focal point.

FIG. 2 shows a portion of a profile of another phase plate bifocal, and its corresponding graph of brightness vs focal power, showing unequal brightnesses (i.e. $B_0^2 \neq B_1^2$) at each focal point.

DESCRIPTION OF THE PREFERRED EMBODIMENTS

Figure 3:
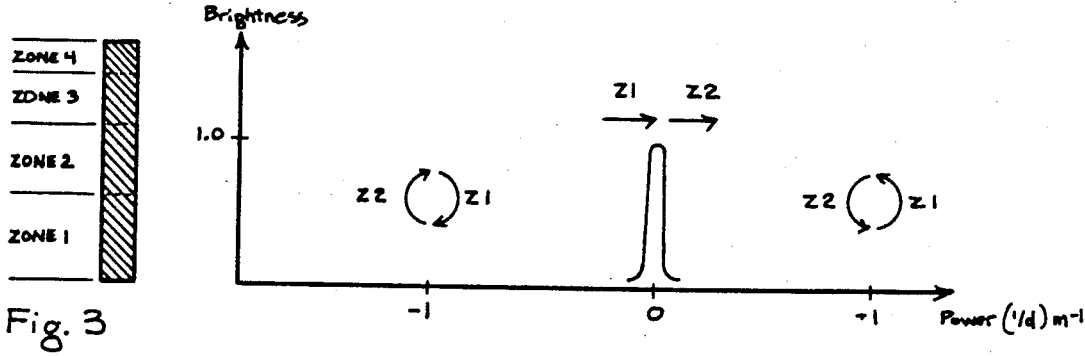
FIG. 3 shows the profile of a flat lens of zero power, and its corresponding graph of brightness vs focal power, showing a single focal point at infinity (i.e. 0.0 Diopters).
Figure 4:
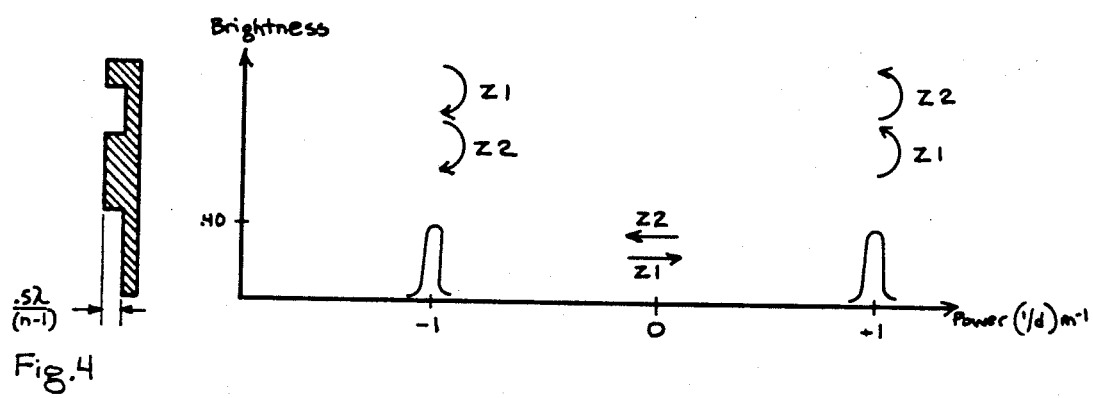
FIG. 4 shows the profile of a flat lens of zero power, modified as described by R. W. Wood, and its corresponding graph of brightness vs focal power, showing two focal points of equal brightnesses.
Figure 5:
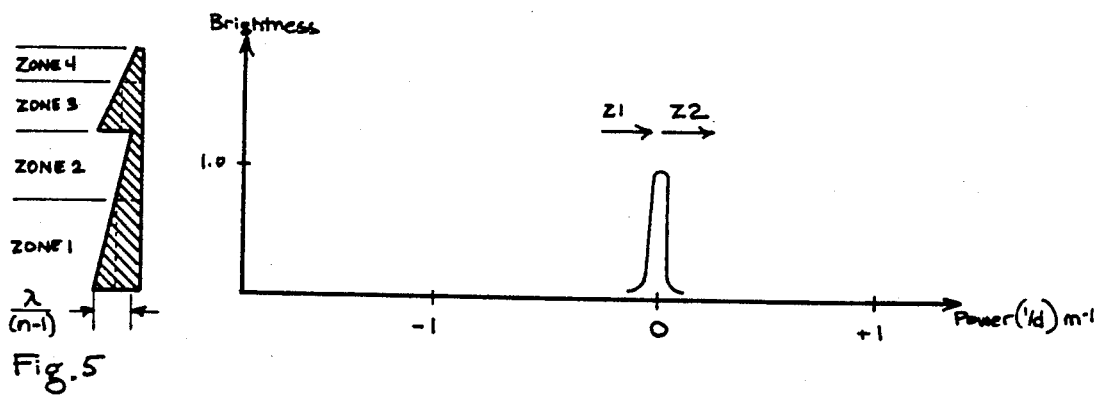
FIG. 5 shows a portion of the profile of a blazed lens with a single focal power, and its corresponding graph of brightness vs focal power, showing the single focal point.
Figure 6:
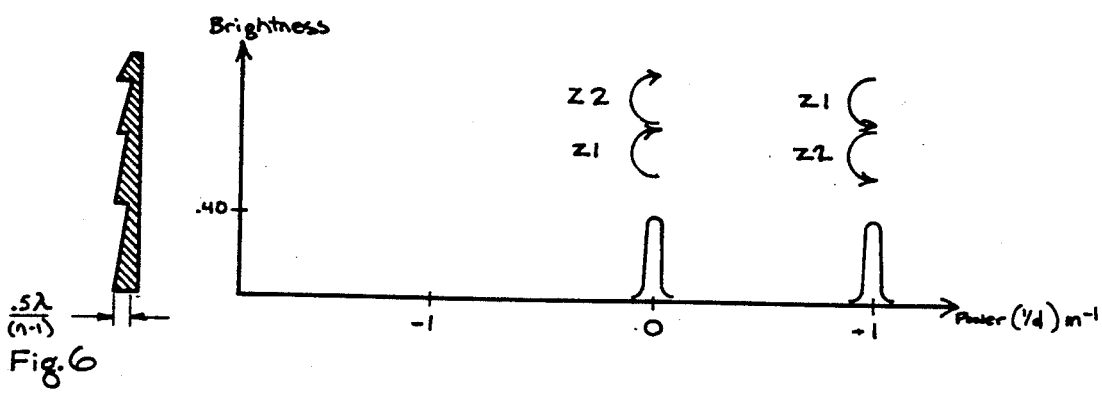
FIG. 6 shows a portion of the profile of the lens of FIG. 5, modified as described by R. W. Wood, and its corresponding graph of brightness vs focal power, showing two focal points of equal brightnesses.
Figure 7A:
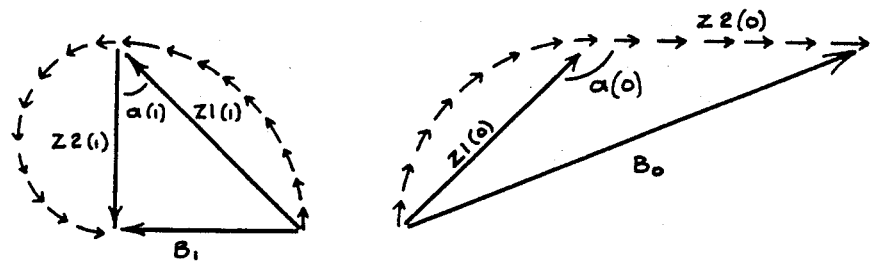
FIG. 7a depicts a geometrical representation of the light amplitude vectors, passing through the annular zones of the lens of FIG. 2.
Figure 7B:
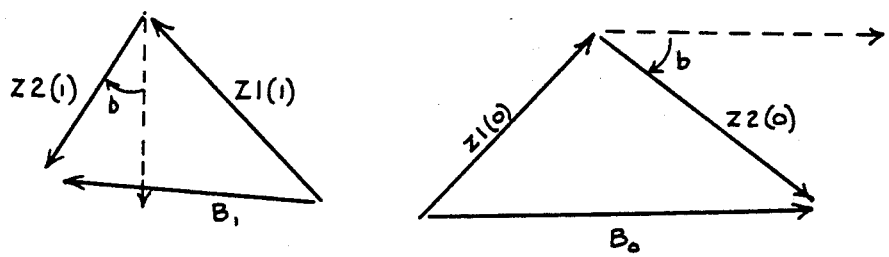
FIG. 7b shows graphically, how the brightnesses $B_0^2$ and $B_1^2$ are altered by introducing a phase shift of b degrees between zone 1 and zone 2.
Figure 7C:
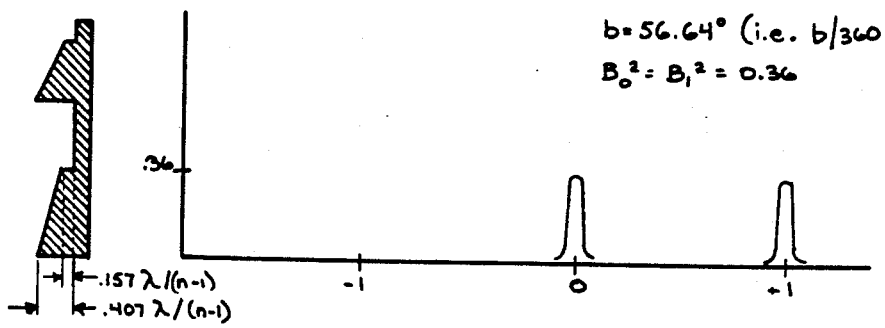
FIG. 7c shows the profile of the lens of FIG. 2, altered according to this invention, so that the image brightnesses are equal at each of the two focii (in particular $B_0^2 = B_1^2 = 0.36$).
Figure 8:
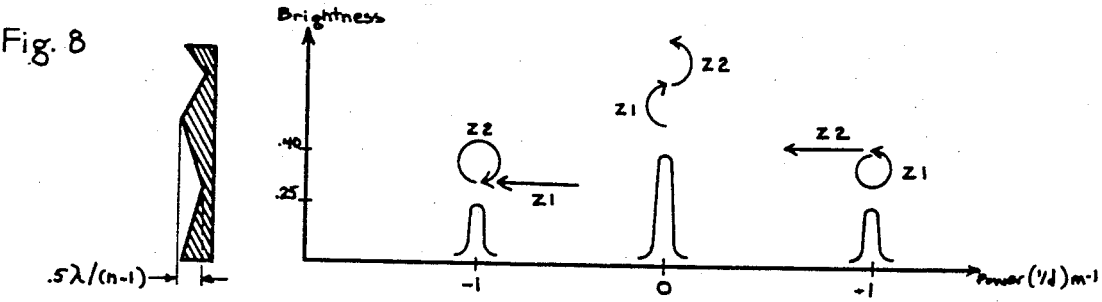
FIGS. 8-14 show portions of profiles of blazed and stepped trifocals, together with their corresponding graphs of brightness vs focal power.
Figure 9:
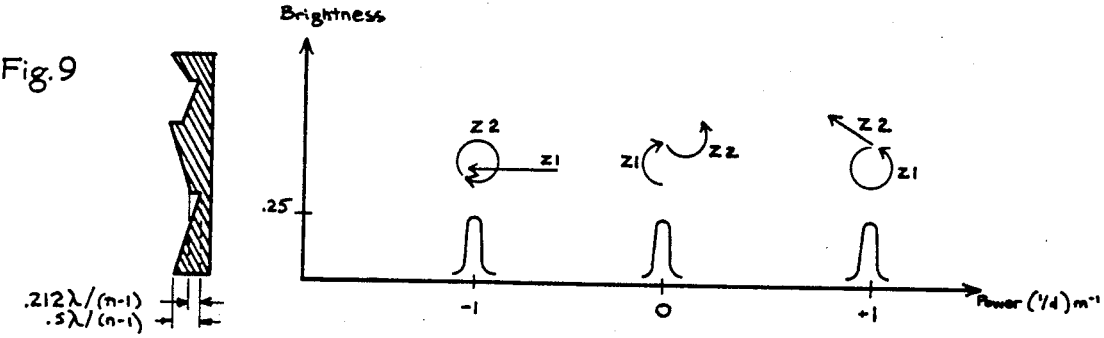
Figure 10:
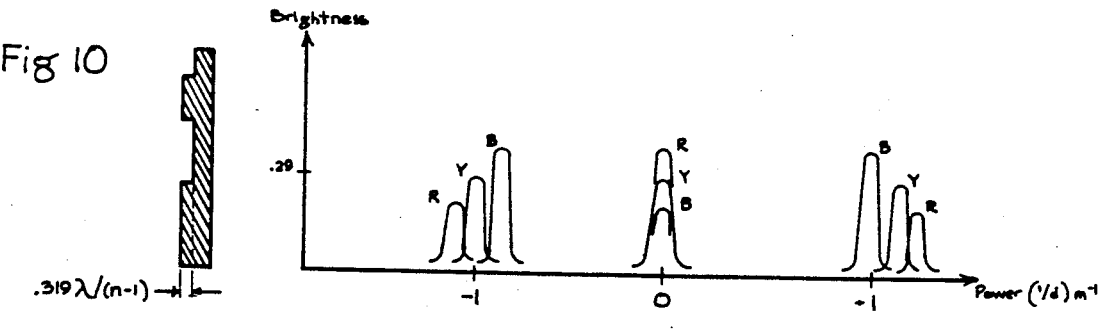
Figure 11:
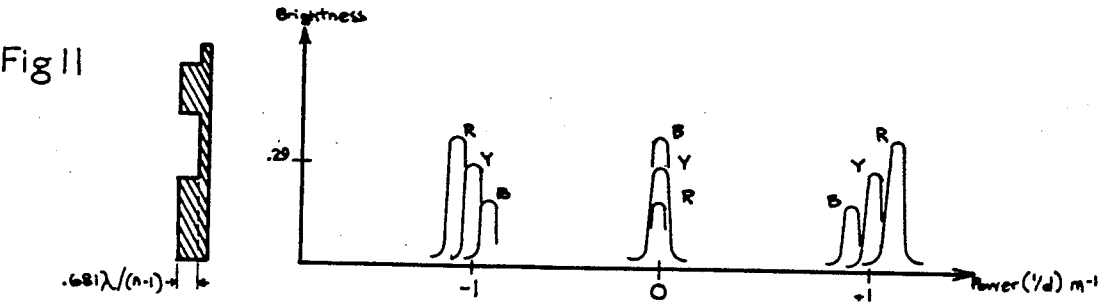
Figure 12:
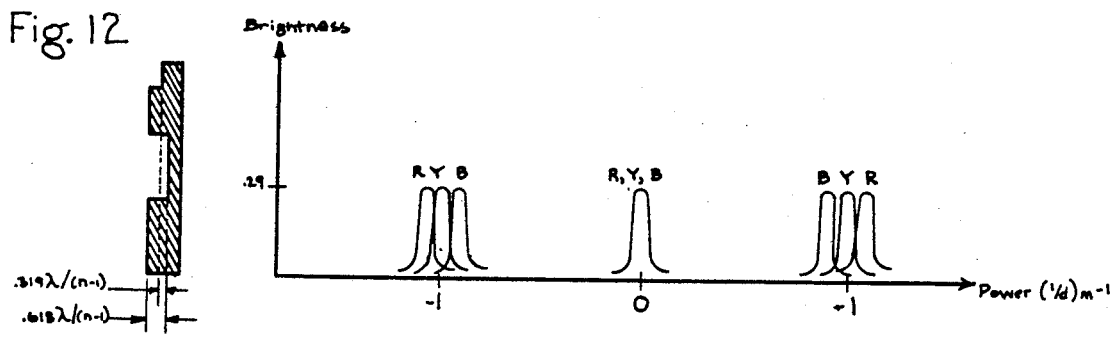
Figure 13:
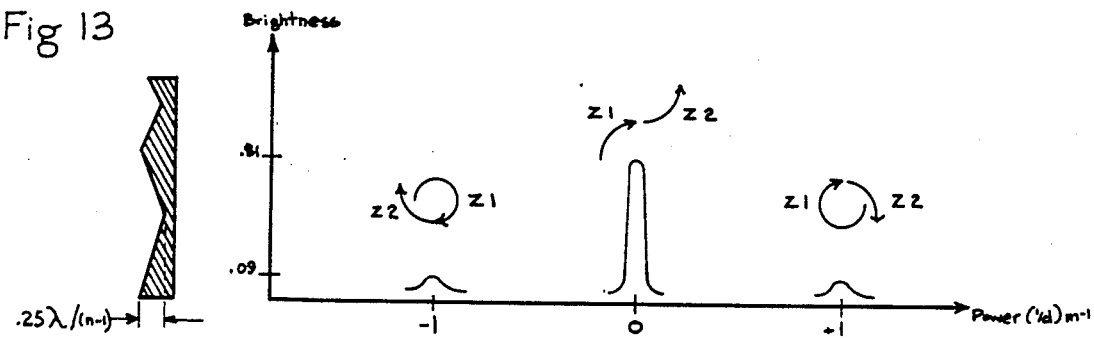
Figure 14:
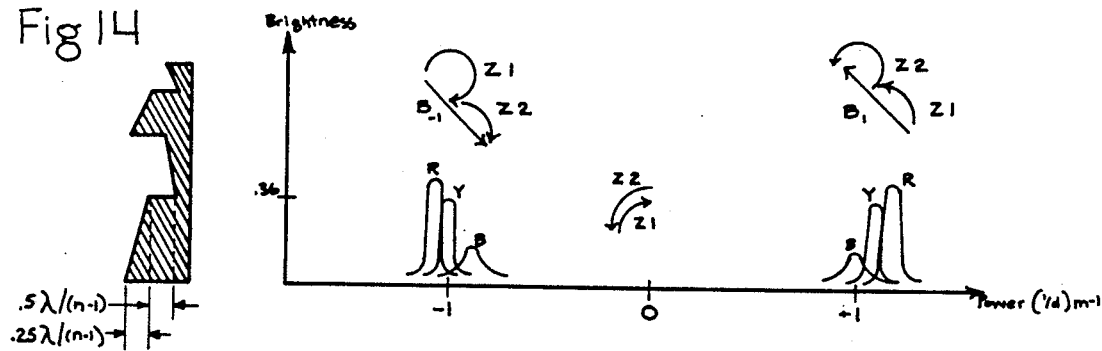
Figure 15:
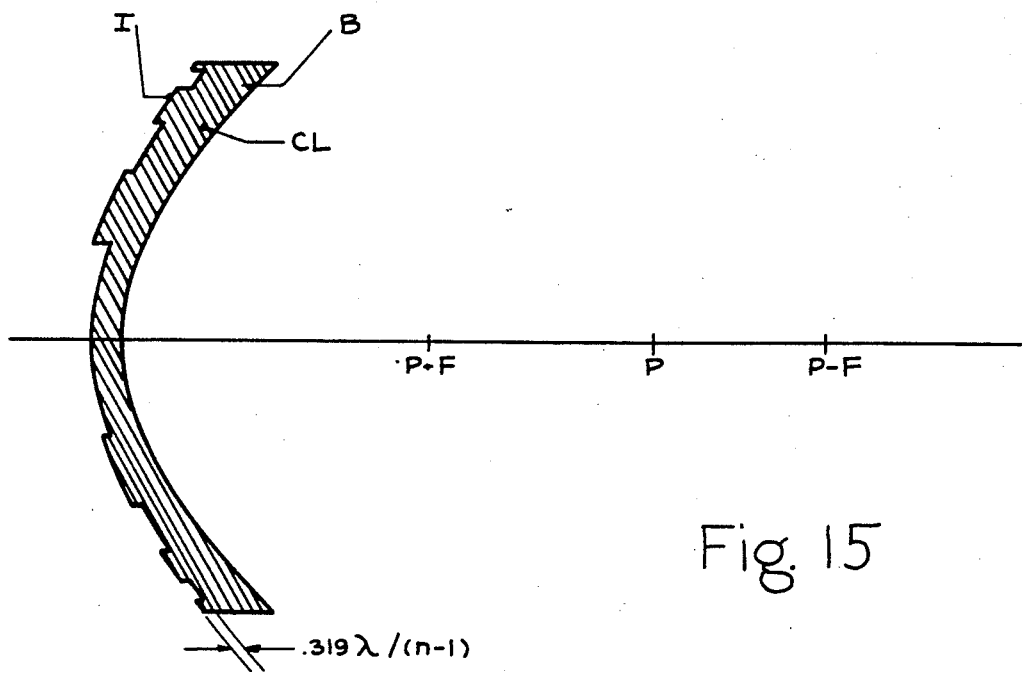
FIG. 15 is a cross-sectional view of a trifocal lens formed by ion reactive etching of steps.

In the embodiment of the invention as shown in FIG. 15, we have by way of illustration, the anterior surface I of a carrier lens or body CL divided into six concentric annular zones, bounded by radii r1-r6, in such a manner as to form a trifocal phase plate. In any actual lens, the number of zones may be more or less, and six zones was chosen merely as an illustrative example. The carrier lens or body of course, is constructed according to the usual principles governing the design of an optical lens with the surfaces I and B either spherical, sphero-cylindrical, or of any other appropriate lens design. The spherical, sphero-cylindrical, or aspheric power P of the carrier lens depends, according to the standard lens formula, on the curvatures of the anterior and posterior surfaces I and B respectively, the center thickness CT, and refractive index n of the carrier lens. These parameters are in turn, determined by the intended use of this trifocal phase plate and the materials available. For example, the posterior surface B may be shaped so as to minimize off axis optical aberrations if this trifocal phase plate is to be used as a spectacle lens. Standard optical materials such as glass, plastic, or any other optical materials, including those used in the manufacture of spectacles, contact lenses, etc. may be used in the fabrication of this and all subsequent embodiments.

In this present configuration alternate annular zones are uniformly etched to a depth of substantially $0.319/(n-1)$ wavelengths of light, where n is the index of refraction of the carrier lens. This will of course, cause a phase shift of 0.319 wavelengths of light between adjacent annular zones. The spacing of the annular zones is of course given by the zone plate formula for r(k). In particular, the radii r(k), demarcating the boundaries between the annular zones are determined by $$r(k) = \sqrt{k*\lambda/F},$$

where $k = 1, 2, 3, \ldots$, $\lambda$ is equal to the wavelength of light under consideration, and F represents the focal power. The resultant trifocal in this case will exhibit three focal powers of equal image brightnesses at $P-F$ Diopters, P Diopters, and $P+F$ Diopters.

The new and important feature of this embodiment, and of all the subsequent embodiments, is the ratio of image brightnesses which are determined by the particular depth of the steps etched into the surface of the lens. The depth in this case is given by $(b/360)*\lambda/(n-1)$ where b is the phase shift in degrees. In this case $b = 114.84$ degrees and was determined as shown in the foregoing text from the equation:

$$z1^2(0) + z2^2(0) - 2*z1(0)*z2(0)*\cos[a(0)+b] = z1^2(1) + z2^2(1) - 2*z1(1)*z2(1)*\cos[a(1)+b].$$

Of course a different value of b would result in a different embodiment of this invention.

Figure 16:
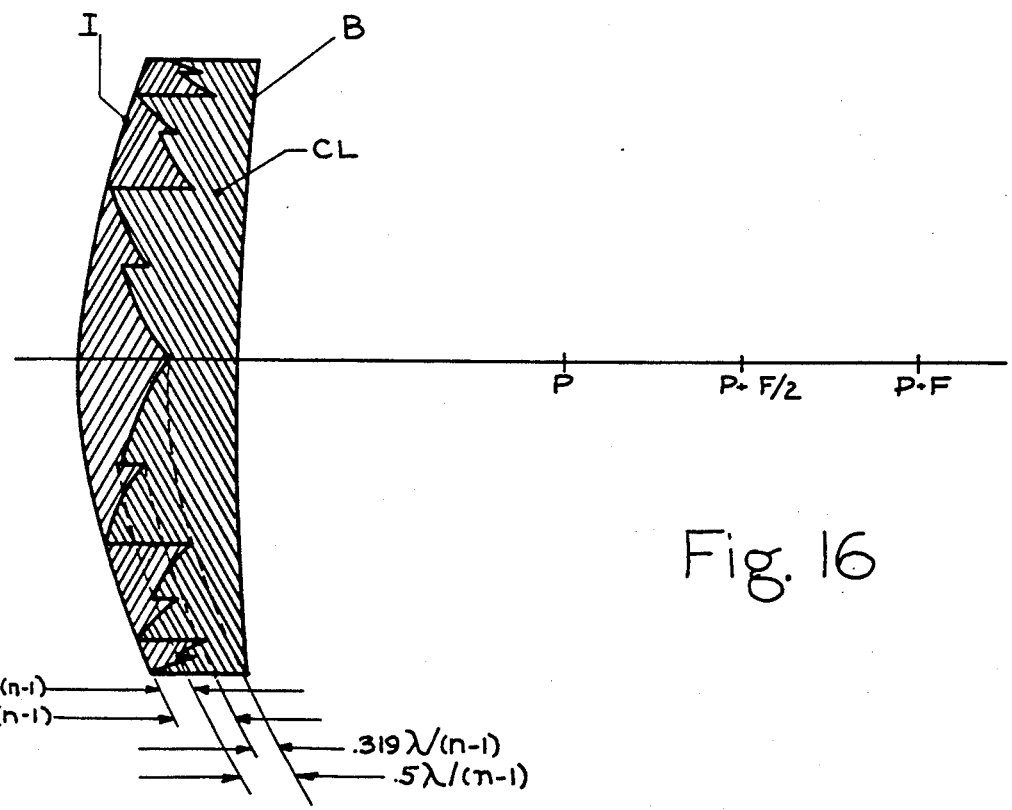
FIG. 16 is a cross-sectional view of a trifocal lens formed by ion implanting of blazed steps.

Another embodiment of the present invention, which utilizes ion implantation, is shown in FIG. 16, where the zones are formed by ions implanted into the surface of the carrier lens CL, thereby changing the index of refraction of the carrier lens from n to n'. Again the depth of implantation is given by the equation $(b/360)*\lambda/(n-n')$. In this case the blazes are $0.5/(n-1)$ wavelengths deep, and the steps are $0.319/(n-1)$ wavelengths deep, where n is the index of refraction of the carrier lens CL. The carrier lens has been designed with a front surface I, a back surface B, and a focal power P. The radii of the annular zones $r(k)$ are determined by the formula $$r(k) = \sqrt{k\lambda/F},$$

with $\lambda$ the design wavelength. The three focal powers of this lens are P, P+F/2, and P+F.

Figure 17:
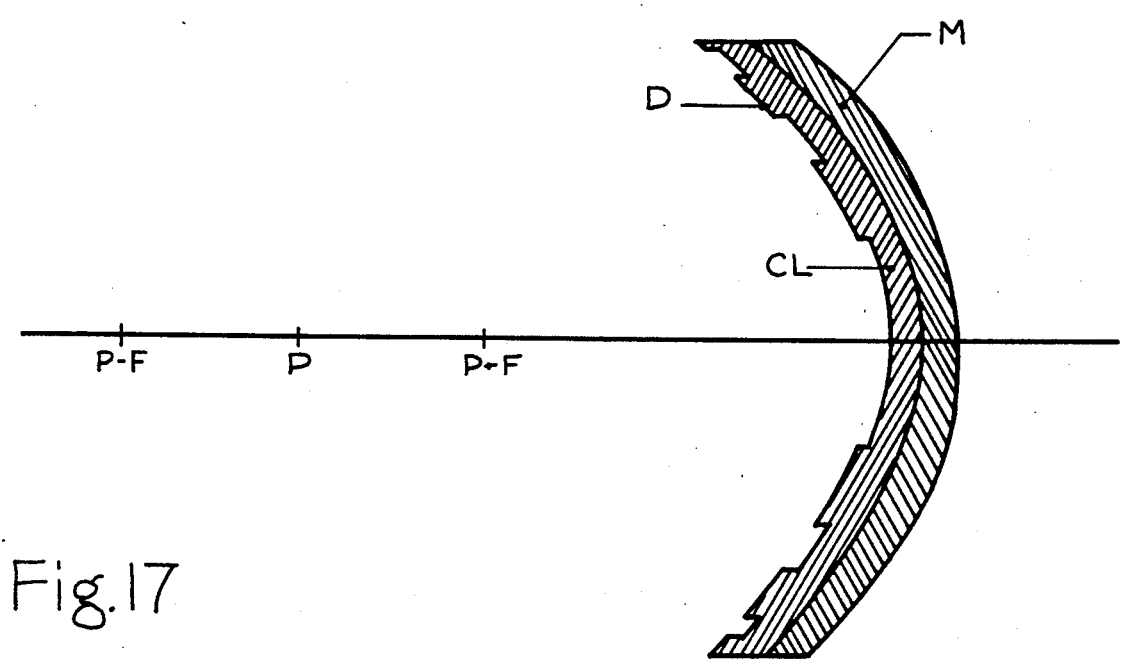
FIG. 17 is a cross-sectional view of a bifocal mirror formed by plating of steps onto the mirror surface.

Another embodiment of the present invention, which utilizes an evaporation plating technique, is shown in FIG. 17, where the zones are formed by the plating of additional material D, onto the surface of the carrier lens CL, thereby increasing the light path through the carrier lens. In this case we see a compound lens-mirror system, the lens CL being bonded to the mirror M, and the thickness of the plating is given by $(b/720)*\lambda/(n'-1)$, with n' the index of refraction of the plated material.

It should be understood, of course, that the foregoing disclosure relates only to the preferred embodiments of the invention, and that numerous modifications or alterations may be made therein, without departing from the spirit and scope of the invention as set forth in the appended claims.

What is claimed is new and desired to be protected by Letters Patent is:

1. A multiple focal point profiled phase plate having a plurality of annular concentric zones spaced according to the formula $$r(k) = \sqrt{constant \times k},$$

where $r(k)$ is the zone radii and k is a zone; in which a repetitive step is incorporated in the profile and has an optical path length greater or less than one-half wavelength.

2. The multiple focal point profiled phase plate of claim 1 wherein the phase plate is part of an optical device containing body means, which body means comprises an optically refracting material.

3. The multiple focal point profiled phase plate of claim 2 wherein a phase shifting means is provided in at least some of the annular zones, the phase shifting means being of a step function nature, causing a substantial constant shift in the optical path length across essentially the entire zone into which it is incorporated.

4. The multiple focal point profiled phase plate of claim 3 wherein the phase shifting means is an excavated portion of the body means.

5. The multiple focal point profiled phase plate of claim 3 wherein the phase shifting means occupies every alternate zone.

6. The multiple focal point profiled phase plate of claim 3 wherein the phase shifting means is adjusted so as to cause equal image brightnesses at each of the focal points of said body means.

7. The multiple focal point profiled phase plate of claim 3 wherein the phase shifting steps are adjusted so as to create a trifocal with equal image brightnesses at each of the focal points of said body means.

8. The multiple focal point profiled phase plate of claim 3 wherein the phase shifting steps are adjusted so as to cause the lens to focus some wavelengths of light preferentially.

9. The multiple focal point profiled phase plate of claim 3 wherein the phase shifting steps are adjusted so as to reduce the maximum depths of any blaze or step.

10. The multiple focal point profiled phase plate of claim 3 wherein the optical device is designed as a contact lens.

11. The multiple focal point profiled phase plate of claim 3 wherein the optical device is designed as a spectacle lens.

12. The multiple focal point profiled phase plate of claim 3 wherein the optical device is designed as an intraocular lens implant.

13. The multiple focal point profiled phase plate of claim 1 wherein the optical device is designed as a mirror.

14. The multiple focal point profiled phase plate of claim 3 wherein the phase shifting means includes the body means together with imbedded contaminants to achieve the desired phase shift.

15. The multiple focal point profiled phase plate of claim 1 wherein the phase plate is designed to operate as a multifocal lens in the visible light range.

16. The multiple focal point profiled phase plate of claim 15 wherein the body means of said phase plate is designed as a contact lens.

17. The multiple focal point profiled phase plate of claim 15 wherein the body means of said phase plate is designed as a camera lens.

* * * * *